US006287543B1

(12) United States Patent
Terren et al.

(10) Patent No.: US 6,287,543 B1
(45) Date of Patent: *Sep. 11, 2001

(54) COMPOSITION ESPECIALLY IN THE FORM OF EMULSION, GEL OR AQUEOUS SOLUTION, INCLUDING A CROSSLINKED POLY (2-ACRYLAMIDO-2-METHYLPROPANESULPHONIC ACID) POLYMER NEUTRALIZED TO AT LEAST 90%

(75) Inventors: Nadia Terren; Sophie Favre, both of Chevilly Larue (FR)

(73) Assignee: L'Oreal, Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/885,798

(22) Filed: Jun. 30, 1997

(30) Foreign Application Priority Data

Jun. 28, 1996 (FR) .................................................. 96 08112

(51) Int. Cl.⁷ .......................... A61K 7/025; A61K 7/031; A61K 7/032
(52) U.S. Cl. .............................. 424/64; 424/63; 424/401; 514/844
(58) Field of Search ..................................... 424/486, 487, 424/63–64, 401, 78.18, 70.16; 514/772.6, 844

(56) References Cited

U.S. PATENT DOCUMENTS

| 3,986,510 | * | 10/1976 | Higuchi et al. . | |
|---|---|---|---|---|
| 4,534,892 | * | 8/1985 | Suzuki et al. . | |
| 4,695,453 | | 9/1987 | Tuominen | 424/81 |
| 4,871,536 | | 10/1989 | Arraudeau | 424/59 |
| 5,034,218 | | 7/1991 | Duvel | 424/70 |
| 5,114,706 | | 5/1992 | Duvel | 424/70 |
| 5,137,728 | * | 8/1992 | Bawa . | |
| 5,470,551 | * | 11/1995 | Dubief et al. . | |
| 5,519,088 | * | 5/1996 | Itoh et al. . | |
| 5,569,683 | * | 10/1996 | Bootman et al. . | |

FOREIGN PATENT DOCUMENTS

| 0 152 095 | 5/1985 | (EP) . |
|---|---|---|
| 1110240 | 4/1968 | (GB) . |
| 4-230310 | 7/1991 | (JP) . |

* cited by examiner

*Primary Examiner*—Edward J. Webmann
(74) *Attorney, Agent, or Firm*—Finnegan, Henderson, Farabow, Garrett & Dunner, L.L.P.

(57) ABSTRACT

The invention relates to a cosmetic, dermatological, hygienic or pharmaceutical composition which is in the form of, or includes, an aqueous gel or an aqueous, hydroalcoholic or multiphase solution additionally including at least one crosslinked poly(2-acrylamido-2-methylpropanesulphonic acid) polymer neutralized to at least 90% and pigments or water-soluble dyes.

19 Claims, No Drawings

COMPOSITION ESPECIALLY IN THE FORM OF EMULSION, GEL OR AQUEOUS SOLUTION, INCLUDING A CROSSLINKED POLY (2-ACRYLAMIDO-2-METHYLPROPANESULPHONIC ACID) POLYMER NEUTRALIZED TO AT LEAST 90%

The subject-matter of the present invention is a cosmetic composition which can take the form of an emulsion and is capable of being employed for the care or make-up of the skin, the semimucosae, the mucosae or the exoskeletal parts.

Cosmetic make-up compositions generally include fatty substances such as oils and waxes and a particulate phase generally made up of fillers and pigments. They can thus be, for example in the case of lip rouges, in the form of a stick or rod or in the form of a flexible paste. Make-up compositions can also include water or a hydrophilic phase and can then be especially in the form of oil-in-water or water-in-oil emulsion, multiple emulsion or aqueous solution or gel, especially when they are a make-up foundation, a tinted cream, a care cream or a sun care product.

It has been found that when these various cosmetic compositions are applied to the skin, the mucosae or the semimucosae, they have the disadvantage of transferring. This means that the composition is liable to be deposited, at least partially, on some substrates with which it comes into contact, such as, for example, a glass, a garment or the skin. On being deposited, the composition leaves a mark on the substrate. This therefore results in a mediocre tenacity of the composition on the skin or the mucosae, resulting in the need to renew its application at regular intervals.

Another disadvantage of these compositions lies in the problem of migration. It has been found, in fact, that some compositions have a tendency to propagate inside small wrinkles or wrinkles of the skin, in the case of foundations; in the small wrinkles which surround the lips, in the case of lip rouges, and in the folds of the eyelid in the case of eye shadows. It has also been found, especially in the case of eye shadows, that streaks appear in the make-up, which are generated by the movements of the eyelids. All these phenomena produce an unaesthetic effect which, quite obviously, the consumer wishes to avoid.

The objective of the present invention is to propose a composition which makes it possible to obtain a film which behaves very well, which does not transfer and which does not stain a substrate with which it might be in contact.

A first subject of the invention is therefore the use of at least one crosslinked poly(2-acrylamido-2-methylpropanesulphonic acid) polymer neutralized to at least 90% in a cosmetic, dermatological, hygienic or pharmaceutical composition in order to limit, reduce or eliminate the transfer or the migration of the said composition, or in order to improve the behavior of the said composition.

Another subject of the invention is the use of such a polymer as an agent making it possible to limit, reduce or eliminate the transfer or the migration of the said composition, or as an agent making it possible to improve the behaviour of the said composition.

Another subject of the invention is a cosmetic, dermatological, hygienic or pharmaceutical composition which is in the form of, or includes, an oil-in-water emulsion, a water-in-oil emulsion, a multiple emulsion or a multiphase solution additionally including at least one crosslinked poly(2-acrylamido-2-methylpropanesulphonic acid) polymer neutralized to at least 90% and pigments.

Yet another subject of the invention is a cosmetic, dermatological, hygienic or pharmaceutical composition which is in the form of, or includes, an aqueous gel or an aqueous, hydroalcoholic or multiphase solution additionally including at least one crosslinked poly(2-acrylamido-2-methylpropanesulphonic acid) polymer neutralized to at least 90% and water-soluble dyes.

Another subject of the invention is a transfer-free make-up or care composition including at least one such polymer.

The invention also has as a subject a process for limiting, reducing, or preventing the transfer of a cosmetic, dermatological, hygienic or pharmaceutical composition, especially a composition for make-up or care of the skin, of the mucosae, of the semimucosae or of the exoskeletal parts, comprising introducing into the composition at least one crosslinked poly(2-acrylamido-2-methylpropanesulphonic acid) polymer neutralized to at least 90%.

It has in addition been found that the compositions according to the invention do not migrate in the course of time.

Furthermore, the compositions such as the products for care, hygiene or make-up which contain the polymer according to the invention spread uniformly over the local surface to be treated; the hair-care compositions spread and are distributed uniformly along the keratinous fibres and do not run onto the forehead, the back of the neck or the face or into the eyes. This is especially due to the polymer employed which, by virtue of its specific properties of its thickening or gelling agent, makes it possible to obtain a very large number of cosmetic formulations containing substrates of different nature.

In addition, the compositions according to the invention withstand the conventional and specific cosmetic active substances, especially hydroxy acids.

Finally, their cosmetic properties are very advantageous: they provide a certain coolness when applied, as well as great softness.

The compositions according to the invention therefore include at least one crosslinked poly(2-acrylamido-2-methylpropanesulphonic acid) polymer neutralized to at least 90%. This crosslinked and practically or completely neutralized poly(2-acrylamido-2-methylpropanesulphonic acid) polymer is generally water-soluble or swellable in water.

These polymers are in general characterized in that they comprise, distributed randomly:

(a) from 90 to 99.9% by weight, relative to the weight of said at least one crosslinked polymer, of units of the following formula (1):

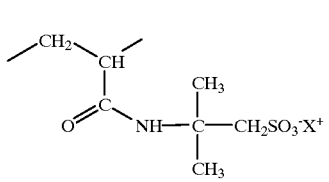

(1)

in which $X^+$ denotes a cation or a mixture of cations, it being possible for at most 10 mol % of the cations $X^+$ to be protons $H^+$, and b) from 0.01 to 10% by weight, relative to the weight of said at least one crosslinked polymer, of crosslinking units originating from at least one monomer containing at least two olefinic double bonds.

The polymers of the invention preferably comprise a number of units of formula (1) in a quantity which is sufficiently large to obtain polymer particles whose hydrodynamic volume in water solution has a radius ranging from 10 to 500 nm and whose distribution is homogeneous and unimodal.

The hydrodynamic volume is determined by the diffusion coefficient D according to Stokes-Einstein according to the method for characterizing a mixture of polymers by laser diffusion, as described in the paper by Chi Wu et al., Macromolecules, 1995, 28, 4914–4919.

The polymers according to the invention which are more particularly preferred include from 98 to 99.5% by weight of units of formula (1) and from 0.2 to 2% by weight of crosslinking units.

The cation $X^+$ denotes a cation or a mixture of cations which are chosen in particular from a proton, an alkali metal cation, a cation equivalent to that of an alkaline-earth metal or the ammonium ion. The preferred cation $X^+$ is the $NH_4^+$ cation. More particularly, 90 to 100 mol % of the cations are $NH_4^+$ cations and 0 to 10 mol % are protons ($H^+$).

The crosslinking monomers which have at least two olefinic double bonds are selected, for example, from dipropylene glycol diallyl ether, polyglycol diallyl ether, triethylene glycol divinyl ether, hydroquinone diallyl ether, tetraallyloxyethanoyl or other allyl or vinyl ethers, polyfunctional alcohol, tetraethylene glycol diacrylate, triallylamine, trimethylolpropane diallyl ether, methylenebisacrylamide or divinylbenzene.

The crosslinking monomers which contain at least two olefinic double bonds are more preferably selected from those corresponding to the following formula (2):

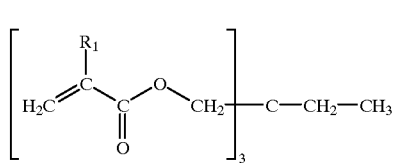

(2)

in which $R_1$ denotes a hydrogen atom or a $C_1$–$C_4$ alkyl radical. The crosslinking monomers are most preferably (trimethylolpropane triacrylate).

The polymerization reaction of the polymers of the invention produces not only linear chains but also branched or crosslinked polymer molecules. These molecules can be characterized especially by their rheological behaviour in water, but more particularly by the dynamic scattering of light.

In the case of the characterization of the molecules by dynamic light scattering, the distribution of the hydrodynamic volume of the polymer structures is measured.

The macromolecules dissolved in water are flexible and surrounded by a solvation shell made up of water molecules. With charged polymers like those of the invention the size of the molecules depends on the quantity of salt in the water. In polar solvents the uniform charge along the polymer's main chain produces a considerable expansion of the polymer chain. The fact of increasing the quantity of salt increases the quantity of electrolyte in the solvent and forms a screen to the polymer's uniform charges. In addition to the molecules carried in the solvation shell, solvent molecules are bound in the cavities of the polymer. In this case the solvent molecules form part of the macromolecules in solution and move at the same average speed. The hydrodynamic volume thus describes the linear dimension of the macromolecule and of these salvation molecules.

The hydrodynamic volume $v_h$ is determined by the following formula:

$$v_h = M/N_A \times (V_2 + dV_1)$$

with:

$N_A$ denoting Avogadro's number,

M is the mass in grams of the undissolved macromolecule, $V_1$ denoting the specific volume of the solvent, $V_2$ denoting the specific volume of the macromolecule, d the mass in grams of the solvent which is associated with 1 gram of undissolved macromolecule.

If the hydrodynamic particle is spherical, it is then easy to calculate the hydrodynamic radius from the hydrodynamic volume using the formula:

$$V_h = 4\pi R^3/3$$

with R denoting the dynamic radius.

The cases where the hydrodynamic particles are perfect spheres are extremely rare. Most of the synthetic polymers involve compact structures or ellipsoids of high eccentricity. In this case the determination of the radius is based on a sphere which is equivalent from a viewpoint of friction to the shape of the particle in question.

As a general rule, work is done on molecular weight distributions and hence on hydrodynamic radius and volume distributions. In the case of polydisperse systems the distribution of the diffusion coefficients must be calculated. From this distribution are deduced the results relating to the radial distribution and to the distribution of the hydrodynamic volumes.

The hydrodynamic volumes of the polymers of the invention are determined in particular by dynamic light scattering from scattering coefficients D according to Stokes-Einstein, from formula: $D = kT/6\pi\eta R$ where K is Boltzmann's constant, T the absolute temperature in degrees Kelvin, $\eta$ is the viscosity of the solvent (water) and R is the hydrodynamic radius.

These scattering coefficients D are measured according to the method for characterizing a mixture of polymers by laser scattering, described in the following references:

(1) Pecora, R.; Dynamic Light Scattering; Plenum Press, New York, 1976;
(2) Chu, B.; Dynamic Light Scattering; Academic: Press, New York, 1994;
(3) Schmitz, K. S.; Introduction to Dynamic Light Scattering; Academic Press, New York, 1990;
(4) Provincher S. W.; Comp. Phys., 27, 213, 1982;
(5) Provincher S. W.; Comp. Phys., 27, 229, 1982;
(6) ALV Laservertriebgesellschaft mbH, Robert Bosch Str. 47, D-63225 Langen, Germany;
(7) ELS-Reinheimer Strasse 11, D-64846 Gross-Zimmern, Germany;
(8) Chi Wu et al., Macromolecules, 1995, 28, 4914–4919.

The polymers which are particularly preferred are those exhibiting a viscosity, measured with the Brookfield viscometer, rotor 4, at a speed of rotation of 100 revolutions/minute, at 25° C. and in aqueous solution at a concentration of 2% by weight, which is higher than or equal to 1000 cP and more preferably ranging from 5000 cP to 40 000 cP and most preferably from 6500 cP to 35 000 cP.

The crosslinked poly(2-acrylamido-2-methylpropanesulphonic acid) polymer according to the invention can be obtained according to the process of preparation including the following stages:

(a) the 2-acrylamido-2-methylpropanesulphonic acid monomer is dispersed or dissolved in free form in a solution of tert-butanol or of water and of tert-butanol, (b) the monomer solution or dispersion obtained in (a) is neutralized with one or several inorganic or organic bases, preferably aqueous ammonia $NH_3$, in a quantity which makes it possible to obtain a degree of neutralization of the sulphonic acid functional groups of the polymer ranging from 90 to 100%, (c) the crosslinking monomer(s) is(are) added to the solution or dispersion obtained in (b), (d) a conventional radical polymerization is performed in the presence of free-radical initiators at a temperature ranging from 10 to 150° C., the polymer precipitating in the tert-butanol-based solution or dispersion.

The crosslinked and practically or completely neutralized poly(2-acrylamido-2-methylpropanesulphonic acid) polymer can be present in the compositions according to the invention in a concentration of from 0.01 to 20% by weight relative to the total weight of the composition, preferably from 0.1 to 5% by weight, and more preferably from 0.4 to 2% by weight.

The compositions of the invention additionally contain a cosmetically, hygienically, pharmaceutically or dermatologically acceptable medium, that is to say a medium which is compatible with all keratinous materials such as the skin, the nails, hair, eyelashes and eyebrows, the mucosae and the semimucosae, and any other cutaneous region of the body and of the face.

The compositions of the invention contain a cosmetically or dermatologically acceptable aqueous medium. In a preferred embodiment the composition according to the invention takes the form of an oil-in-water emulsion. However, it may also take the form of a water-in-oil emulsion, a multiple emulsion, an aqueous gel or an aqueous, hydroalcoholic or multiphase solution, especially water/powder and water/oil/powder.

The aqueous phase of the emulsion according to the invention may include water, a floral water such cornflower water or a mineral water such as VITTEL water, LUCAS water or LA ROCHE POSAY water. This aqueous phase may be present in a content of 15 to 99.5% by weight relative to the total weight of the composition, preferably 40 to 80% by weight when the composition takes the form of oil-in-water emulsion, or preferably 85 to 95% by weight when the composition takes the form of a gel or of an aqueous solution.

In addition, the aqueous phase may include from 0% to 14% by weight, relative to the total weight of the aqueous phase, of a $C_2$–$C_6$ lower monoalcohol or of a polyol such as glycerol, butylene glycol, isoprene glycol, propylene glycol or polyethylene glycol.

The compositions according to the invention may include a fatty phase, especially one consisting of fatty substances which are liquid at 25° C., such as oils of animal, vegetable, mineral or synthetic origin.

When the composition according to the invention takes the form of an emulsion, the said fatty phase may include any cosmetically acceptable oil, insofar as the said oil makes it possible, when mixed with the aqueous phase and the optional additives, to obtain a stable emulsion, that is to say an emulsion that does not break but which remains in the form of a single phase for at least 24. hours after storage at 25° C. without any creaming or oil release phenomenon.

The oils capable of being employed may optionally be volatile. A volatile oil is intended to mean any compound capable of evaporating in contact with the skin. Use is made preferably of oils whose flash point is sufficiently high to allow these oils to be employed in formulation, and sufficiently low to obtain the desired evanescent effect. Oils whose flash point is of the order of 40–100° C. are preferably employed.

Volatile silicone oils may thus be mentioned, such as:
cyclic volatile silicones containing from 3 to 8 silicon atoms, preferably from 4 to 6, such as, cyclotetradimethylsiloxane, cyclopentadimethylsiloxane or cyclohexadimethylsiloxane;

cyclocopolymers of the dimethylsiloxane/methylalkylsiloxane type, such as SILICONE FZ 3109 sold by Union Carbide, which is a dimethylsiloxane/methyloctylsiloxane cyclocopolymer;

linear volatile silicones containing from 2 to 9 silicon atoms, such as, hexamethyidisiloxane, hexylheptamethyltrisiloxane or octylheptamethyltrisiloxane.

Volatile hydrocarbon oils, such as isoparaffins and especially isododecane, may also be mentioned.

Among the nonvolatile oils there may be mentioned:
polyalkyl($C_1$–$C_{20}$)siloxanes, especially those containing trimethylsilyl end groups, preferably those whose viscosity is lower than 0.06 m$^2$/s, such as linear polydimethylsiloxanes and alkylmethylpolysiloxanes such as cetyidimethicone (CTFA name);

silicones modified with aliphatic or aromatic groups, optionally fluorinated, or with functional groups such as hydroxyl, thiol or amine groups;

phenylated silicone oils, especially those of the following formula (3):

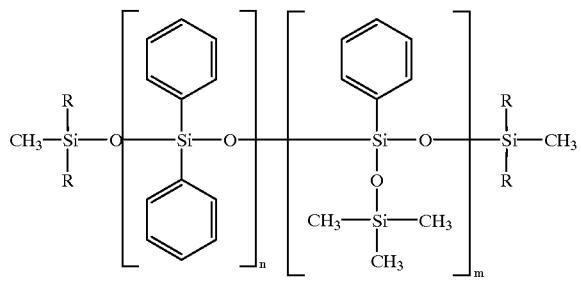

in which R is a $C_1$–$C_{30}$ alkyl radical, an aryl radical or an aralkyl radical, n is an integer from 0 to 100 and m is an integer from 0 to 100, provided that the sum is from 1 to 100;

oils of animal, vegetable or mineral origin, such as liquid paraffin, liquid petrolatum, perhydrosqualene, apricot oil, wheat germ, sweet almond, calophyllum, sesame, macadamia, grape pip, rape, copra, groundnut, palm, castor, avocado, jojoba, olive or cereal germ oils, fatty acid esters, alcohols, acetylglycerides, alcohol or polyalcohol octanoates, decanoates or ricinoleates, fatty acid triglycerides, glycerides and fluorinated and perfluorinated oils.

In a particular embodiment of the invention an emulsion can be prepared including only silicone-containing fatty substances, such as volatile cyclic oils optionally mixed with polydimethylsiloxanes (PDMSS) or phenylated silicone oils or else such as silicone gums, especially phenylated or hydroxylated, mixed with optionally volatile silicone oils.

When the composition takes the form of an oil-in-water emulsion, the fatty phase of the emulsion may be present in a content of 2% to 40% by weight relative to the total weight of the emulsion, preferably from 3% to 30% by weight and most preferably from 3% to 20% by weight.

The composition according to the invention may additionally include other fatty substances which may be selected by the person skilled in the art on the basis of his or her general knowledge, so as to give the final composition the desired properties, for example in respect of consistency, texture or transfer. These additional fatty substances may be waxes, resins or pasty fatty substances of animal, vegetable, mineral or synthetic origin, and mixtures thereof.

There may be mentioned in particular:

silicone resins; and waxes of animal, vegetable, mineral or synthetic origin, such as microcrystalline waxes, paraffin wax, petrolatum, vaseline, ozokerite, montan wax, beeswax, lanolin and its derivatives, candelilla, ouricury, carnauba and Japan waxes, cocoa butter, cork fibre or sugar cane waxes, hydrogenated oils which are solid at 25° C., ozokerites, fatty esters and glycerides which are solid at 25° C., polyethylene waxes and the waxes obtained by Fischer-Tropsch synthesis, hydrogenated oils which are solid at 25° C., lanolins, fatty esters which are solid at 25° C., silicone waxes and fluorinated waxes.

The composition according to the invention may additionally include one or several cosmetically acceptable organic solvents determined by acceptable tolerance, toxicology and feel. These organic solvents may represent from 0% to 98% of the total weight of the composition. They may be chosen from hydrophilic organic solvents, lipophilic organic solvents, amphiphilic solvents and mixtures thereof.

Among the hydrophilic organic solvents there may be mentioned, for example, linear or branched lower monoalcohols containing from 1 to 8 carbon atoms, like ethanol, propanol, butanol, isopropanol and isobutanol, polyethylene glycols, containing from 6 to E80 ethylene oxides, polyols such as propylene glycol, isoprene glycol, butylene glycol, glycerol and sorbitol, isosorbide mono- or dialkyl in which the alkyl groups contain from 1 to 5 carbon atoms, glycol ethers like diethylene glycol monomethyl or monoethyl ether and propylene glycol ethers like dipropylene glycol methyl ether.

Among the amphiphilic organic solvents, mention may be made, for example, of polyols such as polypropylene glycol (PPG) derivatives, for instance polypropylene glycol esters of fatty acid, and PPG ethers of fatty alcohol, for instance PPG-36 oleate, PPG-23 oleyl ether. Lipophilic organic solvents which may be mentioned, for example, are fatty esters such as diisopropyl adipate, dioctyl adipate and alkyl benzoates.

When the composition according to the invention takes the form of an emulsion, it may optionally additionally include a surfactant, although this is not necessary for obtaining a stable and fine emulsion.

It may also include 0 to 5% by weight, relative to the total weight of the emulsion, of at least one coemulsifier which may be selected from oxyethylenated sorbitan monostearate, fatty alcohols such as stearyl alcohol or cetyl alcohol, or polyol fatty acid esters such as glyceryl stearate.

In addition, the emulsion according to the invention may include one or more thickening agents in preferred concentrations ranging from 0 to 6% by weight, relative to the total weight of the emulsion. The thickening agent may be selected from:

polysaccharide biopolymers such as xanthan gum, carob gum, guar gum, alginates, modified celluloses such as hydroxyethyl cellulose, methyl cellulose, hydroxypropyl cellulose and carboxymethyl cellulose;

synthetic polymers such as polyacrylic acids, for example, glyceryl poly(meth)acrylate polymers such as HISPAGEL or LUBRAGEL from Hispano Quimica or Gardian, polyvinylpyrrolidone, polyvinyl alcohol, crosslinked acrylamide and ammonium acrylate polymers such as PAS 5161 or BOZEPOL C from Hoechst, acrylate/octylacrylamide copolymers such as DERMACRYL from National Starch, polyacrylamide-based polymers such as SEPIGEL 305 from Seppic, and crosslinked acrylamide and methacryloyloxyethyltrimethylammonium chloride polymers such as SALCARE SC 92 from Allied Colloids; and magnesium aluminium silicate.

In addition, it has been found that, astonishingly, the polymers according to the invention make it possible to prepare aqueous gels and emulsions in a wide pH range, especially of acidic pH lower than 7, while keeping their viscosity which is stable in time at ambient temperature or at higher temperatures. Thus, the composition according to the invention may include at least one acidic compound, i.e., at least one compound whose solution or aqueous dispersion has a pH lower than or equal to 7.

Among these acidic compounds hydroxy acids and $\alpha$- and $\beta$-ketoacids may be mentioned in particular. The hydroxy acids employed in accordance with the present invention are preferably selected from $\alpha$-hydroxyacids, n-octanoyl-5-salicylic acid or salicylic acid.

The $\alpha$-hydroxyacids to which the invention applies may be linear, branched or cyclic, saturated or unsaturated. The hydrogen atoms of the carbon chain may additionally be substituted by halogens or halogenated, alkylated, acylated, acyloxylated, alkoxycarbonylated or alkoxylated radicals containing from 2 to 28 carbon atoms. The $\alpha$-hydroxyacid which can be employed according to the invention may consist of a mono- or polycarboxylic acid containing one or more hydroxyl functional groups, at least one of these hydroxyl functional groups having to occupy an $\alpha$ position on the acid. The $\alpha$-hydroxyacids of the invention are preferably $\alpha$-hydroxyalkanoic acids containing from 2 to 18 carbon atoms.

As $\alpha$-hydroxyacids which can be employed in the invention there may be preferably mentioned glycolic, lactic, malic, tartaric, citric, mandelic, $\alpha$-hydroxycaprylic, $\alpha$-hydroxyhexanoic, $\alpha$-hydroxydecanoic, $\alpha$-hydroxydodecanoic, $\alpha$-hyd roxytetradecanoic, $\alpha$-hydroxyhexadecanoic, $\alpha$-hydroxyoctadecanoic, $\alpha$-hydroxyeicosanoic, $\alpha$-hydroxydocosanoic, $\alpha$-hydroxyhexacosanoic and $\alpha$-hydroxyoctacosanoic acids.

It is also possible to mention ascorbic acid, kojic acid, caffeic acid, salicylic acid and its derivatives, as well as any natural or synthetic compounds containing such acids, like plant extracts and more especially fruit extracts.

The acidic compounds may be present in the composition of the invention in contents of 0 to 10% by weight, relative to the total weight of the composition, preferably from 0.2% to 5% by weight.

The composition according to the invention may include a particulate phase which may include pigments or pearlescent pigments or fillers usually employed in cosmetic compositions. Pigments should be understood to mean white or colored, inorganic or organic particles which are insoluble in the mixture and intended to color or opacify the composition. Fillers should be understood to mean colorless or white, mineral or synthetic, lamellar or nonlamellar particles intended to impart softness, mattness and uniformity to the make-up. Pearlescent pigments should be understood to mean iridescent particles which reflect the light.

The pigments may be present in a proportion of 0–20% by weight relative to the total weight of the composition, and preferably in a proportion of 2–15%. They may be white or colored, mineral or organic, of usual or nanometric size. Titanium, zirconium or cerium dioxides and zinc, iron or chromium oxides, nanotitanates and ferric blue may be mentioned among the mineral pigments and nanopigments. Carbon black and barium, strontium, calcium and aluminium lakes may be mentioned among the organic pigments.

When the composition takes the form of an oil-in-water emulsion, the pigments are preferably hydrophobic or are made hydrophobic, i.e., they can be treated so as to make their surface hydrophobic. This treatment may be performed according to the methods which are known to a person skilled in the art. The pigments may in particular be coated with silicone compounds such as PDMS or with polymers, especially polyethylenes. MAPRECOS SA pigments or MYOSHI PI pigments may thus be mentioned.

It has been found, in fact, that when the pigments are not coated, the product obtained has a nonsmooth or breaking appearance. The pigments are preferably present in the fatty phase of the emulsion.

When the composition takes the form of a solution or of an aqueous gel, it may include water-soluble dyes selected from the usual dyes of the field in question, such as Ponceau disodium salt, alizarin green disodium salt, quinoline yellow, amaranth trisodium salt, tartrazine disodium salt, rhodamine monosodium salt, fuchsine disodium salt and xanthophyll.

The pearlescent pigments may be present in the composition in a proportion of 0–20% by weight, preferably in a high content of the order of 2–15% by weight. Among the pearlescent pigments which can be envisaged there may be mentioned natural mother of pearl, mica coated with titanium oxide, with iron oxide, with natural pigment or with bismuth oxychloride, as well as colored titanium mica.

The fillers, which may be present in the composition in a proportion of 0–20% by weight, relative to the total weight of the composition, preferably 2–10%, may be mineral or synthetic, lamellar or nonlamellar. Talc, mica, silica, kaolin, nylon and polyethylene powders, TEFLON, starch, boron nitride, microbeads such as EXPANCEL (Nobel Industrie), polytrap (Dow Corning) and silicone resin microbeads (for example TOSPEARLS from Toshiba) may be mentioned.

The composition may additionally include any additives usually employed in the field of cosmetics, such as antioxidants, dyes, especially water-soluble ones, perfumes, essential oils, preserving agents, cosmetic active substances, moisturizers, vitamins, essential fatty acids, sphingolipids, self-tanning compounds such as DHA, sunscreens, liposoluble polymers, especially hydrocarbons, such as polybutene and polyalkylenes, polyacrylates and silicone polymers compatible with fatty substances.

A person skilled in the art will obviously take care to choose this or these additional optional compounds or their quantity, so that the advantageous properties of the composition according to the invention are not, or substantially are not, damaged by the envisaged incorporation.

These additives may be present in the composition in a proportion of 0–10% by weight.

The compositions according to the invention may be in any of the appropriate forms for a topical application, especially in the form of serum, lotion, cream, milk, aqueous gel, emulsions obtained by dispersing a fatty phase in an aqueous phase (O/W) or vice versa (W/O), of liquid or semiliquid or even pasty or solid consistency.

The emulsions according to the invention may form all or part of a cosmetic, pharmaceutical or hygienic composition.

The compositions according to the invention find an application especially in the field of make-up of the skin, of the semimucosae, of the mucosae or of the exoskeletal parts, and are then, for example, in the form of a foundation, a blusher or eye shadow, a lip rouge, a mascara or an eyeliner.

They can also be employed as a care base for the lips or as a care product for the skin, the mucosae, the semimucosae or the exoskeletal parts, a hygienic or pharmaceutical product or else a sun or self-tanning product.

They also find an application in the hair-care field, especially as gels or creams for care of the exoskeletal parts such as hair, eyelashes and eyebrows or else as an aqueous gel, especially for hair styling.

The examples which follow illustrate the invention without being limiting in nature.

EXAMPLE OF PREPARATION A OF THE POLYMER

Into a 5-liter round bottom flask fitted with a stirrer, a reflux condenser, a thermometer and a conducting device for nitrogen and for aqueous ammonia were introduced 2006.2 g of tert-butanol and then 340.0 g of 2-acrylamido-2-methylpropanesulphonic acid, which were dispersed in the solution with vigorous stirring. After 30 minutes aqueous ammonia was added through the upper conduit of the round bottom flask and the reaction mixture was kept for 30 minutes at ambient temperature until a pH of the order of 6–6.5 was obtained. 32.0 g of a solution of trimethylolpropane triacrylate at a concentration of 25% in tert-butanol were introduced next and heating to 60° C. was applied while the reaction mixture was simultaneously made inert by introducing nitrogen into the flask. Once this temperature was reached, dilauroyl peroxide was added. The reaction started immediately, which was reflected in a temperature rise and in a precipitation of the polymerizate. Fifteen minutes after the polymerization began, a stream of nitrogen was introduced. Thirty minutes after the addition of the initiator the temperature of the reaction mixture reached a maximum of 65–70° C. Thirty minutes after having reached this temperature it is heated to reflux and kept in these conditions for 2 hours. The formation of a thick paste was observed during the reaction.

The product obtained was cooled to ambient temperature and filtered off. The paste recovered was next dried under vacuum at 60–70° C. for 24 hours. 391 g of crosslinked and neutralized poly(2-acrylamido-2-methylpropanesulphonic acid) were obtained, with a viscosity, measured with the Brookfield viscometer, rotor 4, at a speed of rotation of 100 revolutions/minute in a water solution at a concentration of 2% and at 25° C., ranging from 15,000 cP to 35,000 cP. The viscosity of the polymer may be chosen and controlled by conventional means as a function of the envisaged cosmetic application.

EXAMPLE OF PREPARATION B OF THE POLYMER

Into a 5-liter round bottom flask fitted with a stirrer, a reflux condenser, a thermometer and a conducting device for nitrogen and for aqueous ammonia were introduced 2006.2 g of tert-butanol and then 340.0 g of 2-acrylamido-2-methylpropanesulphonic acid, which were dispersed in the solution with vigorous stirring. After 30 minutes aqueous ammonia was added through the upper conduit of the round bottom flask and the reaction mixture was kept for 30 minutes at ambient temperature until a pH of the order of 6–6.5 was obtained. 19.2 g of a solution of trimethylolpropane triacrylate at a concentration of 25% in tert-butanol were introduced next and heating to 60° C. was applied while the reaction mixture was simultaneously made inert by introducing nitrogen into the flask. Once this temperature was reached, dilauroyl peroxide was added. The reaction started immediately, which was reflected in a temperature rise and in a precipitation of the polymerisate. Fifteen minutes after the beginning of the polymerization, a stream of nitrogen was introduced. Thirty minutes after the addition of the initiator the temperature of the reaction mixture reached a maximum of 65–70° C. Thirty minutes after having reached this temperature it was heated to reflux and kept in these conditions for 2 hours. The formation of a thick paste was observed during the reaction.

The product obtained was cooled to ambient temperature and filtered off. The paste recovered was next dried under vacuum at 60–70° C. for 24 hours. 391 g of crosslinked and neutralized poly(2-acrylamido-2-methylpropanesulphonic acid) were obtained, with a viscosity, measured with the Brookfield viscometer, rotor 4, at a speed of rotation of 100 revolutions/minute in a water solution at a concentration of 2% and at 25° C., of the order of 7000 cP.

Composition Example 1

A foundation was prepared which had the following composition:

| | |
|---|---|
| iron and titanium oxides coated with PDMS | 10 g |
| crosslinked poly(2-acrylamido-2-methylpropane-sulphonic acid) neutralized with aqueous ammonia, prepared according to the process of Example A, with a viscosity at 25° C. of 16,000 cP in aqueous solution at a concentration of 2% | 1 g |
| hydroxylated silicone resin in PDMS | 16 g |
| stabilizers | q.s. |
| water | q.s. 100 g |

The aqueous phase was heated so as to dissolve the stabilizers and the polymer was dispersed therein; the pigments were dispersed in the fatty phase and this fatty phase was introduced into the aqueous phase at ambient temperature with stirring.

A foundation was thus obtained which spread easily on the skin without a greasy feel and did not transfer in contact with a fabric. This foundation imparted a certain feeling of coolness when being applied to the skin.

Composition Example 2

A make-up gel which had the following composition was prepared:

| | |
|---|---|
| iron and titanium oxides coated with PDMS | 7 g |
| crosslinked poly(2-acrylamido-2-methylpropane-sulphonic acid) neutralized with aqueous ammonia, prepared according to the process of Example A, with a viscosity at 25° C. of 16,000 cP in aqueous solution at a concentration of 2% | 1.5 g |
| mixture of silicone resin and of volatile silicone (polydiphenyldimethylsiloxane + cyclopentadimethylsiloxane) | 16 g |
| aqueous solution of α-hydroxyacids (49% solids content) | 1 g |
| stabilizers | q.s. |
| triethanolamine | q.s. pH 3.5 |
| water | q.s. 100 g |

A stable emulsion which had a pH of 3.5 was obtained, which made it possible to obtain a uniform and natural make-up. The product was cool on application and easy to apply. A sensation of softness was obtained at the outcome. The composition behaved well and did not transfer.

Example 3

Study of the Persistence Properties of the Emulsions as a Function of the Nature of the Fatty Phase Various emulsions (foundation) in accordance with the invention were produced, each emulsion differing in the nature of the fatty phase.

The emulsions were prepared according to the following compositions:

| | |
|---|---|
| fatty phase | X g |
| PDMS-coated pigments | 10 g |
| crosslinked poly(2-acrylamido-2-methylpropane-sulphonic acid) neutralized with aqueous ammonia, prepared according to the process of Example A, with a viscosity at 25° C. of 16,000 cP in aqueous solution at a concentration of 2% | 1 g |
| water | q.s. 100 g |

The compositions were prepared in the usual way by mixing the ingredients of the fatty phase and the predispersed pigments; the aqueous phase was prepared by mixing water and the polymer and then heating to 80° C.; the two phases were mixed at ambient temperature with stirring using a turbine.

The persistence properties of these emulsions were determined next. To do this, 0.05 g of each emulsion were applied to an area of 50 cm$^2$ on the forearm and the composition applied was then allowed to dry for 5 minutes.

A strip of polyester fabric was next applied over the portion of the treated forearm. The strip was moved, with the aid of an apparatus, with a vertical translation motion in contact with the treated forearm. The fabric was kept stretched with a counterweight, thus creating a friction of the fabric during the translation.

Ten to-and-fro rubbing movements were carried out. The colored marks which may have been deposited on the fabric were next scored according to the following scale:

Highly stained fabric: score=0

Trace-free fabric: score=10.

A foundation is considered to transfer little when the mark is equal to or higher than 8.5.

The results obtained are reported in the table below.

TABLE I

| Fatty phase | Content (X) in grams | Score (1 to 10) |
|---|---|---|
| Hydroxylated silicone resin in PDMS (Q2-1403 from Dow Corning) | 25 | 9.5 |
| | 16 | 9.5 |
| Polydiphenyldimethylsiloxane resin in cycloD5 (15/85) | 25 | 9.5 |
| Polydimethylsiloxane (viscosity 10 cSt) | 12 | 10 |
| Phenylated silicone oil (DC556 from Dow Corning) | 16 | 9.5 |
| Apricot almond oil | 25 | 8.5 |
| Isostearyl neopentanoate | 12 | 10 |
| Mixture Q2-1403 + apricot oil | 8 + 8 | 9 |

TABLE I-continued

| Fatty phase | Content (X) in grams | Score (1 to 10) |
|---|---|---|
| Mixture Q2-1403 + isostearyl neopentanoate | 8 + 8 | 9 |
| | 5 + 11 | 9.5 |
| | 14 + 11 | 8.5 |
| Mixture PDMS 10 cSt + Q2-1403 | 12.5 + 12.5 | 9 |

It is clear from the above results that the emulsions according to the invention exhibited good persistence properties and did not transfer onto the fabric.

This was also the case when oils of vegetable origin, or fatty esters, were present in the composition.

What is claimed is:

1. A cosmetic, dermatological, hygienic or pharmaceutical composition in the form of an oil-in-water emulsion, a water-in-oil emulsion, a multiple emulsion, an aqueous gel, an aqueous hydroalcoholic solution or a multiphase solution, comprising at least one crosslinked poly(2-acrylamido-2-methylpropanesulphonic acid) polymer neutralized to at least 90% and additionally comprising pigments or water-soluble dyes, wherein said composition is in the form of a make-up product for the skin, the semimucosae or the exoskeletal parts and is a foundation, a blusher, an eye shadow, a lip rouge, a mascara or an eyeliner.

2. A composition according to claim 1, wherein said at least one crosslinked poly(2-acrylamido-2-methylpropanesulphonic acid) polymer comprises, randomly distributed:
   (a) from 90 to 99.9% by weight, relative to the weight of said at least one crosslinked polymer, of units of the following formula (1):

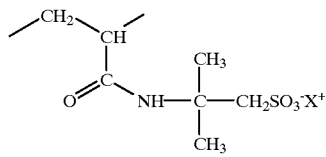

in which $X^+$ denotes a cation or a mixture of cations it being possible for at most 10 mol % of the cations $X^+$ to be protons $H^+$, and
   (b) from 0.01 to 10% by weight, relative to the weight of said at least one crosslinked polymer, of crosslinking units originating from at least one monomer containing at least two olefinic double bonds.

3. A composition according to claim 2, wherein said at least one crosslinked poly(2-acrylamido-2-methylpropanesulphonic acid) polymer contains from 98 to 99.5% by weight of units of formula (1) and from 0.2 to 2% by weight of crosslinking units.

4. A composition according to claim 2, wherein said cation is selected from a proton, an alkali metal cation, a cation equivalent to that of an alkaline-earth metal and an ammonium ion.

5. A composition according to claim 2, wherein said at least one monomer containing at least two olefinic double bonds is dipropylene glycol diallyl ether, polyglycol diallyl ether, triethylene glycol divinyl ether, hydroquinone diallyl ether, tetraallyloxyethanoyl or another allyl or vinyl ether, a polyfunctional alcohol, tetraethylene glycol diacrylate, triallylamine, trimethylolpropane diallyl ether, methylenebisacrylamide or divinylbenzene.

6. A composition according to claim 2, wherein said crosslinking units originating from at least one monomer correspond to the following formula (2):

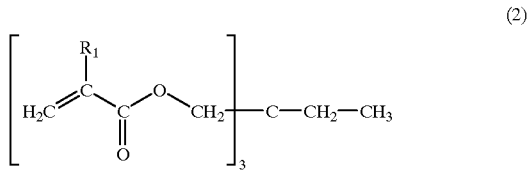

in which $R_1$ denotes a hydrogen atom or a $C_1$–$C_4$ alkyl radical.

7. A composition according to claim 1, wherein said at least one crosslinked poly(2-acrylamido-2-methylpropanesulphonic acid) polymer exhibits a viscosity, measured with the Brookfield viscometer. rotor 4, at a speed of rotation of 100 revolutions/minute, at 25° C. and in aqueous solution at a concentration of 2% by weight, greater than or equal to 1000 cP.

8. A composition according to claim 7, wherein said at least one crosslinked poly(2-acrylamido-2-methylpropanesulphonic acid) polymer exhibits a viscosity ranging from 5000 cP to 40,000 cP.

9. A composition according to claim 8, wherein said at least one crosslinked poly(2-acrylamido-2-methylpropanesulphonic acid) polymer exhibits a viscosity ranging from 6500 cP to 35,000 cP.

10. A composition according to claim 1, wherein said at least one crosslinked poly(2-acrylamido-2-methylpropanesulphonic acid) polymer is present in a concentration ranging from 0.01 to 20% by weight relative to the total weight of the composition.

11. A composition according to claim 10, wherein said at least one crosslinked poly(2-acrylamido-2-methylpropanesulphonic acid) polymer is present in a concentration ranging from 0.1 to 5% by weight relative to the total weight of the composition.

12. A composition according to claim 11, wherein said at least one crosslinked poly(2-acrylamido-2-methylpropanesulphonic acid) polymer is present in a concentration ranging from 0.4 to 2% by weight relative to the total weight of the composition.

13. A composition according to claim 1, wherein the aqueous phase of said oil-in-water emulsion, water-in-oil emulsion, multiple emulsion, aqueous gel, aqueous hydroalcoholic solution or multiphase solution represents an amount ranging from 15 to 99.5% by weight relative to the total weight of the composition.

14. A composition according to claim 1, wherein said composition contains said pigments in an amount ranging from 2–15% by weight relative to the total weight of the composition.

15. A composition according to claim 14, wherein said pigments are titanium dioxide, zirconium dioxide, cerium dioxide, zinc oxide, iron oxide, chromium oxide, nanotitanium, ferric blue, carbon black, barium lake, strontium lake, calcium lake, aluminum lake, or mixtures of any of the foregoing.

16. A composition according to claim 1, wherein said composition additionally contains a $C_2$–$C_6$ lower monoalcohol, a polyol or mixtures thereof.

17. A composition according to claim 1, wherein said composition additionally comprises a fatty phase comprising at least one oil of animal, vegetable, mineral or synthetic origin or at least one silicone resin.

18. A composition according to claim 1, wherein said composition additionally comprises at least one acidic compound.

19. A composition according to claim 1, wherein said composition contains said water-soluble dyes, wherein said water-soluble dyes are Ponceau disodium salt, alizarin green disodium salt, quinoline yellow, amaranth trisodium salt, tartrazine disodium salt, rhodamine monosodium salt, fuchsine disodium salt, xanthophyll, or mixtures of any of the foregoing.

* * * * *

UNITED STATES PATENT AND TRADEMARK OFFICE
CERTIFICATE OF CORRECTION

PATENT NO.   : 6,287,543 B1                                           Page 1 of 1
DATED        : September 11, 2001
INVENTOR(S)  : Nadia Terren et al.

It is certified that error appears in the above-identified patent and that said Letters Patent is hereby corrected as shown below:

Column 13, claim 2,
Line 44, after "mixture of cations" a comma should be inserted.

Column 14, claim 7,
Line 18, "viscometer." should read -- viscometer, --.

Signed and Sealed this

Twelfth Day of March, 2002

Attest:

JAMES E. ROGAN
Attesting Officer       Director of the United States Patent and Trademark Office